US008812082B2

(12) United States Patent
Hajicek et al.

(10) Patent No.: US 8,812,082 B2
(45) Date of Patent: Aug. 19, 2014

(54) AUTOMATICALLY SUPPLYING A PRESSURIZING UNIT OF A MEDICAL INJECTION DEVICE WITH FLUID

(75) Inventors: David Hajicek, Minnetonka, MN (US); Richard Oftedahl, Jordan, MN (US)

(73) Assignee: ACIST Medical Systems, Inc., Eden Prairie, MN (US)

( * ) Notice: Subject to any disclaimer, the term of this patent is extended or adjusted under 35 U.S.C. 154(b) by 1413 days.

(21) Appl. No.: 12/261,713

(22) Filed: Oct. 30, 2008

(65) Prior Publication Data

US 2010/0113924 A1 May 6, 2010

(51) Int. Cl.
*A61M 5/00* (2006.01)
*A61M 1/00* (2006.01)
*A61M 5/36* (2006.01)

(52) U.S. Cl.
CPC . *A61M 5/36* (2013.01); *A61M 5/00* (2013.01); *A61M 1/00* (2013.01); *A61M 5/007* (2013.01)
USPC .......................................... 600/432; 604/123

(58) Field of Classification Search
CPC ........... A61M 5/36; A61M 5/00; A61M 1/00; A61M 5/007
USPC ......................................................... 600/432
See application file for complete search history.

(56) References Cited

U.S. PATENT DOCUMENTS

| 5,573,515 | A | 11/1996 | Wilson et al. |
| 6,221,045 | B1 | 4/2001 | Duchon et al. |
| 6,626,862 | B1 | 9/2003 | Duchon et al. |
| 6,932,242 | B2 | 8/2005 | Gerlach et al. |
| 7,128,729 | B2 | 10/2006 | Duchon et al. |
| 7,678,072 | B2 | 3/2010 | Weber |
| 2003/0028145 | A1* | 2/2003 | Duchon et al. ................. 604/151 |
| 2007/0100282 | A1* | 5/2007 | Small et al. .................... 604/151 |
| 2008/0161757 | A1* | 7/2008 | Nayak et al. .................... 604/82 |

FOREIGN PATENT DOCUMENTS

| EP | 1 847 284 A1 | 10/2007 |
| WO | 01/74421 A1 | 10/2001 |
| WO | 2006/044409 A2 | 4/2006 |
| WO | WO 2007/033103 A1 | 3/2007 |
| WO | WO 2007/062315 A3 | 5/2007 |

OTHER PUBLICATIONS

Communication from European associate regarding responding to the communication dated Jun. 14, 2011, under Rules 161/162, filed with the European Patent Office for European Patent Application No. 09744569.6-2319, dated Dec. 21, 2011, 20 pgs.

(Continued)

*Primary Examiner* — Tse Chen
*Assistant Examiner* — Hien Nguyen
(74) *Attorney, Agent, or Firm* — Shumaker & Sieffert, P.A.

(57) ABSTRACT

In general, this disclosure relates to techniques for automatically supplying a pressurizing unit (e.g., syringe) that is used with a powered medical fluid injection device with fluid. An example method performed by the medical fluid injection device includes obtaining operational state information of the medical fluid injection device, wherein the operational state information includes information other than a fluid delivery amount for a subsequent injection procedure. The example method further includes using the operational state information to determine whether the powered medical fluid injection device permits a fluid replenishment operation for the pressurizing unit. If the fluid replenishment operation is permitted, the method further includes automatically supplying the pressurizing unit with an amount of medical fluid. If the device includes multiple pressurizing units, the device may initiate an automatic fluid replenishment procedure for one or more of the pressurizing units during operation.

30 Claims, 10 Drawing Sheets

(56) References Cited

OTHER PUBLICATIONS

International Preliminary Report on Patentability for international application No. PCT/US2009/062384, dated Feb. 7, 2011, 11 pp.
Office Action from Australian Application No. 2009314380, dated May 10, 2012, 2 pp.
Reply to Written Opinion, filed with the IPEA/EPO in corresponding PCT Application No. PCT/US2009/062384, on Aug. 30, 2010 (11 pgs).
Notification of Transmittal of the International Search Report and the Written Opinion of the International Searching Authority, or the Declaration from corresponding PCT Application No. PCT/US2009/062384, mailed Mar. 19, 2010 (12 pages).
"ACIST CVi Contrast Delivery System User Manual", ACIST Medical Systems, Inc., Nov. 2005, (91 pages).
First Office Action (with English Translation) and Search Report for corresponding Chinese patent application No. 200980144656.8, dated Nov. 2, 2012, 12 pages.
Examination Report for corresponding Canadian patent application No. 2,741,702, dated Jan. 11, 2013, 2 pages.
Office Action from corresponding Korean Application No. 10-2011-7011092, with translation, dated Sep. 26, 2012, 7 pp.
Examiner's Opinion stated in the Office Action for corresponding Japanese patent application No. 2011-534715, 1 page, Oct. 30, 2012.
Response to Examiner's Report dated May 10, 2012, for corresponding Australian patent application No. 2009314380, dated May 30, 2013, 16 pages.
Response to Examiner's Report dated Jan. 11, 2013, for corresponding Canadian application No. 2,741,702, dated Jul. 11, 2013.
Office Action (with English Translation) for corresponding Korean patent application No. 10-2011-7011092, dated Mar. 26, 2013, 6 pages.

* cited by examiner

US 8,812,082 B2

AUTOMATICALLY SUPPLYING A PRESSURIZING UNIT OF A MEDICAL INJECTION DEVICE WITH FLUID

TECHNICAL FIELD

This disclosure generally relates to the use of pressurizing units, such as syringes, within powered medical fluid injection devices.

BACKGROUND

Medical fluid injection devices are typically used to inject medical fluid into a patient. These devices often include one or more reservoirs to hold the medical fluid, and one or more pressurizing units to inject the medical fluid into the patient. For example, a contrast media powered injection device may include a reservoir containing contrast media and a syringe that is used to inject the contrast media into the patient. The contrast media injection device may be used during certain medical procedures, such as an angiographic or computed tomography (CT) procedure.

Many medical fluid injection devices include one or more syringes to inject fluid. A syringe has a chamber for holding the fluid and a plunger that is moveable within the chamber. The fluid is typically drawn into the chamber from a fluid reservoir when the plunger is moved in a first direction. The fluid is then expelled from the chamber and into the patient, via a catheter, when the plunger is moved in a second, opposite direction. The fluid is delivered at a rate that may be determined by a speed of movement of the plunger.

During a given medical procedure, a medical fluid injection device may need to deliver a determined amount of medical fluid. If the pressurizing unit, such as a syringe, does not contain a sufficient amount of fluid for the procedure, a clinician may need to interact with the device to initiate a fluid replenishment operation. For example, the clinician may push a button or otherwise interact with a graphical user interface (GUI) provided by the device to partially or completely fill the pressurizing unit. In other cases, the device may be capable of calculating or otherwise determining an amount of fluid remaining within the pressurizing unit, and then supplying the pressurizing unit with fluid if it determines that this remaining amount is less than the amount that is required to perform an injection procedure for a patient.

SUMMARY

In general, this disclosure relates to techniques for automatically supplying a pressurizing unit (e.g., syringe) that is used with a medical fluid injection device with medical fluid. If the medical fluid injection device includes multiple pressurizing units, the device may initiate an automatic fluid replenishment procedure for one or more of the pressurizing units during operation, as will be described in more detail below. By automatically supplying a pressurizing unit with fluid at identified times, the device is capable of preventing the pressurizing unit from running empty during a medical procedure. The device may be capable of initiating a fluid replenishment operation without having to know or calculate an amount of fluid required for an injection procedure. As a result, a user of the device, such as a clinician, may not need to interact with the device to initiate a fluid replenishment cycle. In addition, there may be fewer interruptions during a given medical procedure, and there may be opportunities to perform a greater number of procedures in a given time period due to higher operational efficiency of the device.

In one embodiment, an example method performed by a powered medical fluid injection device includes obtaining operational state information of the medical fluid injection device, wherein the operational state information includes information other than a fluid delivery amount for a subsequent injection procedure. The example method further includes using the operational state information to determine whether the powered medical fluid injection device will permit a fluid replenishment operation for a first pressurizing unit. If the fluid replenishment operation is permitted, the method further includes automatically supplying the first pressurizing unit with an amount of medical fluid.

In one embodiment, an example medical fluid injection device includes a first pressurizing unit and an injector head that is configured to obtain operational state information of the device and use the operational state information to determine whether a fluid replenishment operation is permitted for the first pressurizing unit, the operational state information including information other than a fluid delivery amount for a subsequent injection procedure. If the fluid replenishment operation is permitted, the medical fluid injection device supplies the first pressurizing unit with an amount of medical fluid.

The details of one or more embodiments are set forth in the accompanying drawings and the description below. Other features, objects, and advantages will be apparent from the description and drawings, and from the claims.

DETAILED DESCRIPTION

Figure 1A:
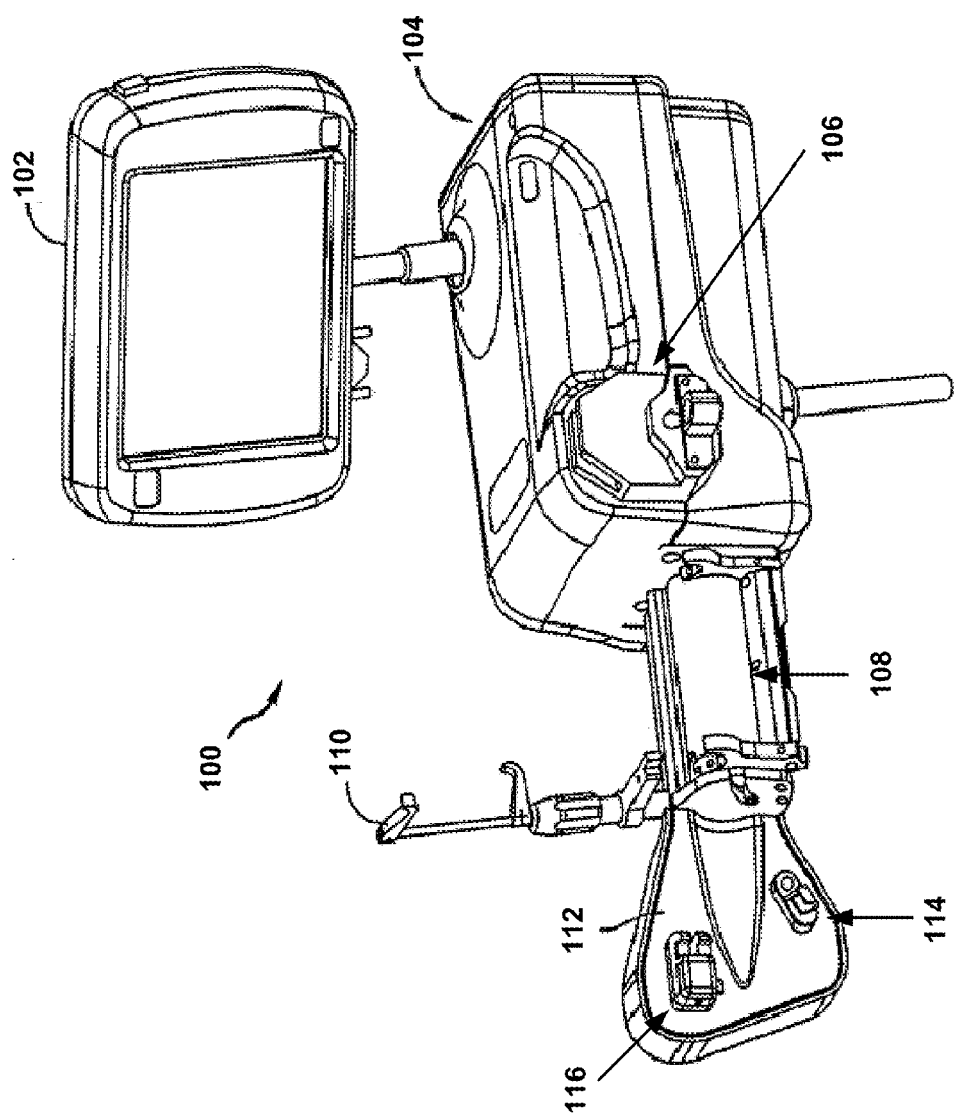
FIG. 1A is a perspective diagram of one embodiment of a powered medical fluid injection device that may be used to automatically supply a pressurizing unit with fluid.
Figure 3:
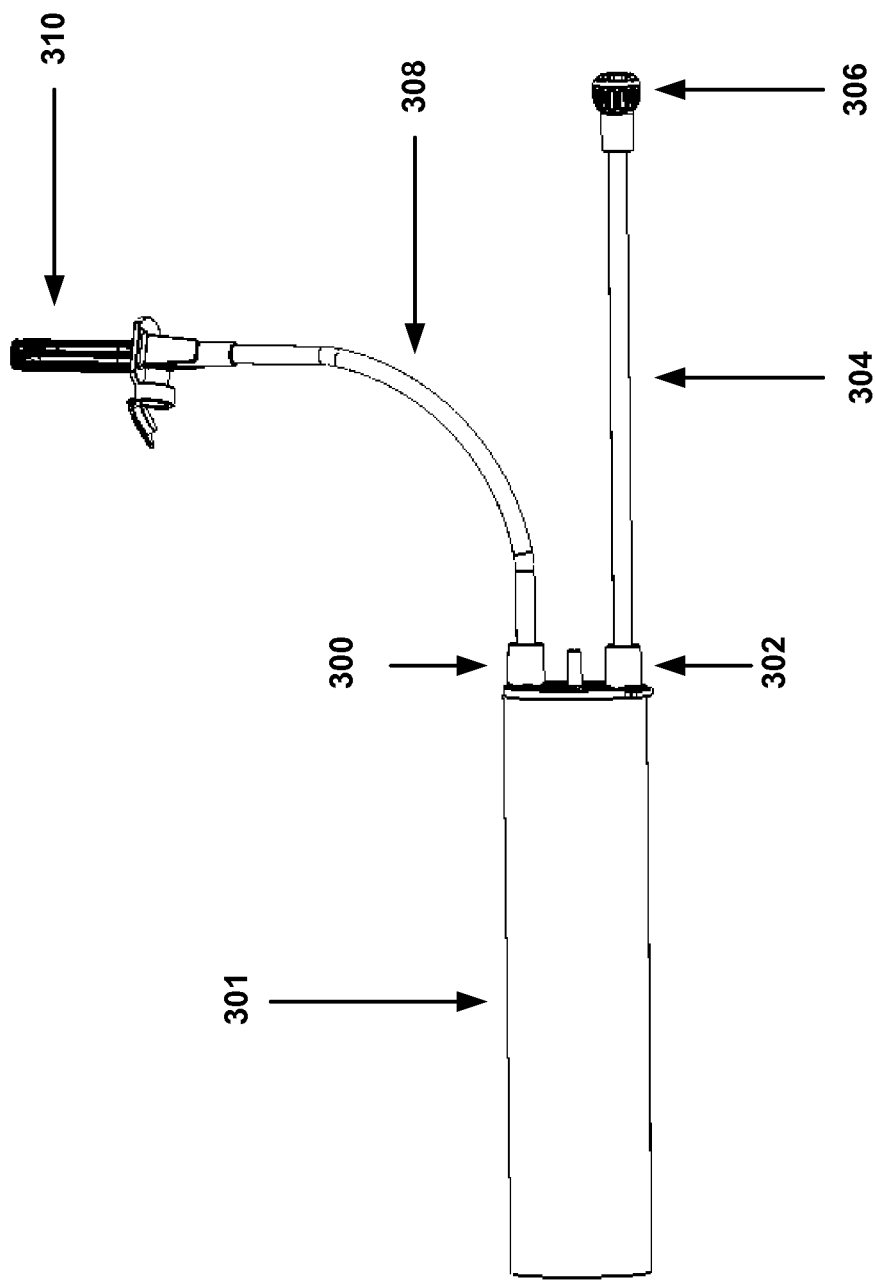
FIG. 3 is a perspective diagram of an example syringe that may be used with a powered medical fluid injection device, according to one embodiment.

FIG. 1A is a perspective diagram of one embodiment of a powered medical fluid injection device 100 that may be used to automatically supply a pressurizing unit contained within a sleeve 108 with medical fluid. In the embodiment of FIG. 1A, the pressurizing unit within sleeve 108 is a syringe. In other embodiments, other forms of pressurizing units may be used, including other types of positive displacement pumps. Device 100 is, in some embodiments, used to inject medical fluid, such as contrast media or saline, into a patient during a medical procedure, such as an angiographic or computed tomography (CT) procedure. Device 100 includes a control panel 102, an injector head 104, a sleeve 108 to hold a pressurizing unit, a reservoir holder 110, a module 112, a patient manifold sensor 114, and an air detector 116. Injector head 104 includes a pump 106 and also includes one or more processors used to control and/or monitor injector head 104, control panel 102, the pressurizing unit within sleeve 108, patient manifold sensor 114, and air detector 116 of device 100. Reservoir holder 110 is capable of holding a fluid reservoir that contains an amount of fluid to be drawn into the syringe during operation of device 100. For example, reservoir holder 110 may hold a reservoir of contrast media or diluent. A second reservoir holder (not shown) may hold a diluent (e.g., saline) for use in pump 106. FIG. 3 shows an example of a syringe that may be used within sleeve 108, according to one embodiment. Patient manifold sensor 114 may, in some cases, be connected to a patient manifold, as will be described in reference to FIG. 1B.

An operator of device 100, such as a clinician, may use control panel 102 to set up various parameters and/or protocols to be used for a given injection procedure. For example, the operator may interact with control panel 102 to enter injection parameters for flow rate, maximum injection volume, maximum injection pressure, rise time, or other parameters. In one embodiment, control panel 102 includes a touch-screen panel.

Pump 106 is capable of pumping fluid. In one embodiment, pump 106 is a peristaltic pump. In this embodiment, tubing and a fluid reservoir (not shown) are coupled to and through pump 106. Pump 106 pumps fluid from the fluid reservoir through the tubing towards module 112. In the example of FIG. 1A, both pump 106 and the syringe contained within sleeve 108 are capable of delivering fluid from device 100 into a catheter. Pump 106 is driven by a motor that is part of pump 106, and the plunger within the syringe is driven by a motor assembly, including an actuator, that is part of injector head 104. In one embodiment, injector head 104 includes a processor that drives the motor assembly.

In one embodiment, reservoir holder 110 holds a fluid reservoir that is coupled to input fluid tubing. This input fluid tubing is coupled to the syringe, such that when the plunger within the syringe is moved in a first direction by the motor, fluid is drawn from the reservoir into the syringe. The syringe within sleeve 108 is further coupled to output tubing. When the plunger within the syringe is moved in a second, opposite direction, fluid is expelled out of the syringe into the output tubing. In one embodiment, the syringe is a dual-port syringe, such that the input tubing is coupled to one port of the syringe, and the output tubing is coupled to another port of the syringe. FIG. 3 shows an example of such a dual-port syringe, which will be described in more detail below.

Patient manifold sensor 114 is coupled to a manifold valve (not shown), according to one embodiment. This manifold valve controls flow of fluid from tubing coupled to either the syringe in sleeve 108 or pump 106. In one embodiment, the manifold valve is coupled to output tubing from the syringe and also to tubing that runs through pump 106. Tubing also is coupled between the manifold valve and air detector 116. After passing through air detector 116, the tubing is then coupled to a patient line or catheter (not shown), such that fluid can ultimately be delivered from device 100 to a patient.

The manifold valve held by the patient manifold sensor 114 is capable of controlling the flow of fluid from the syringe and pump 106 to an external catheter. In one embodiment, the manifold valve has a first position that allows only fluid from the syringe to be delivered to the catheter. The manifold valve has a second position that allows only fluid from pump 106 to be delivered to the catheter. In one embodiment, the manifold valve may comprise a spring-biased spool valve, but in other embodiments, other types of valves, including check valves, may also be used. Patient manifold sensor 114 can detect the manifold valve position and report this position to injector head 104 for safety purposes.

Device 100 also includes air detector 116. Tubing that runs from device 100 to an external catheter passes through air detector 116, which is capable of detecting air bubbles or air columns within the tubing. If air detector 116 detects a measureable or otherwise significant amount of air within the tubing, it is capable of generating an alarm signal for injector head 104. In such a case, a warning or alarm message may be displayed to the operator on control panel 102, indicating that air has been detected. In addition, in one embodiment, device 100 may automatically pause, or terminate, a fluid injection procedure if air detector 116 has detected air in the tubing, such that the air is not delivered to the catheter.

Because device 100 may be used for many injections and patient procedures, injection fluids may need to be continuously replaced. For example, when the reservoir held by holder 110 becomes empty, it may need to be manually replaced with a new (full) reservoir by the operator. In addition, the syringe in sleeve 108 may need to be supplied with injection fluid from time to time, such that there is sufficient fluid within the syringe to perform injections for patient procedures. When an operator detects that a fluid volume within the syringe has decreased or is low, the operator may initiate a manual fluid replenishment procedure by touching a button on or otherwise interacting with control panel 102. By doing so, the operator may manually supply the syringe with fluid contained in the reservoir, either partially or completely.

In addition, device 100 is capable of automatically supplying the syringe, in certain situations, with a determined amount of medical fluid. In one such situation, device 100 may determine a maximum amount of fluid that is to be delivered during an injection procedure. For example, device 100 may determine this amount based upon volume information input by the operator using control panel 102. Device 100 may further determine an amount of fluid remaining in the syringe, such as by making a calculation of remaining fluid volume based upon amounts of fluid injected from the syringe. If the amount remaining in the syringe is less than a maximum amount of fluid to be delivered during an injection procedure, device 100 can cause injector head 104 to add fluid to the syringe.

In one embodiment, injector head 104 of device 100 utilizes operational state information for device 100 in determining whether or not a fluid replenishment operation is permitted for the syringe in sleeve 108. This operational state information may comprise many different types of state information, but may include information other than an amount or volume of fluid that is to be delivered from the syringe for a subsequent injection procedure. That is, injector head 104 of device 100 need not necessarily know how much fluid may need to be delivered from the syringe during an injection procedure in order to determine whether or not to initiate a fluid replenishment operation. Instead, injector head 104 may utilize other operational state information in order to make such a determination.

Operational state information may include information describing operating states or conditions of various portions of a fluid injection device, such as device 100. Examples of operational state information may include, but are not limited to, information related to any combination of the following operational states: (1) currently delivering/injecting fluid from a pressurizing unit (e.g., "injecting") (yes/no); (2) currently delivering fluid from a pump (yes/no); (3) armed (yes/ no); (4) setup complete (yes/no); (5) air present (yes/no); (6) valve position (e.g., spool valve) set to a specified position (positional value); (7) pressurizing unit/syringe full; and (8) auto fluid supply mode (on/off). As these examples illustrate, operating state information may, in some cases, have a finite, relatively small number of values associated with certain states. For example, the state of "currently delivering/injecting fluid from the pressurizing unit" can only have a value of Yes or No. It is possible that some types of operational state information can have more than 2 values for a given operational state. For example, a three-position switch may have any of three different state values, and a valve having more than two possible positions may also have multiple different state values (depending on the position of the valve). The operational state information could thus be used to define a logic table (e.g., a set of rules) that determines, for a given combination of operating states or conditions, whether a fluid replenishment operation is permitted, and may also automatically initiate such a replenishment operation. Each pressurizing unit (e.g., syringe, pump) that is used within the device may have its own associated operational state information.

For example, if injector head 104 uses operational state information to determine that device 100 is currently delivering fluid from pump 106 but not from the syringe contained in sleeve 108, injector head 104 may use this state information to determine that it is permitted to automatically supply the syringe with medical fluid, if necessary (provided that the auto fluid supply mode parameter is set to "on"). That is, if the syringe is not currently delivering fluid, injector head 104 may cause the syringe to be supplied with fluid. If the syringe is currently full, injector head 104, of course, would not need to initiate a fluid replenishment procedure. But, if the syringe is not full, injector head 104 may actuate a motor/actuator assembly coupled to the syringe to supply the syringe with a determined amount of fluid. In one scenario, injector head 104 may decide to completely fill the syringe to capacity. Thus, if the syringe is a 100 milliliter (ml) syringe and is currently half full of medical fluid, injector head 104 may fill syringe to a full 100 ml capacity. In one scenario, injector head 104 may only partially fill the syringe with fluid.

In one embodiment, a known or determined amount of fluid may be supplied to the syringe during a replenishment operation. In one embodiment, device 100 may cause replenishment of the syringe when the amount remaining in the syringe is below the maximum amount of fluid to be delivered during an injection procedure by a threshold amount (e.g., to limit excessive fluid replenishment operations). In one embodiment, replenishing of the syringe with fluid may occur when the amount of fluid remaining in the syringe is less than a certain level (or less than a specified amount of remaining fluid), e.g., when the amount remaining in the syringe is less than a determined percentage of the capacity of the syringe, or less than a determined percentage of the maximum amount. User-selectable parameters may be used to specify threshold amounts or determined percentages.

In one embodiment, device 100 may dynamically terminate a fluid replenishment procedure of the syringe if the operational state of device 100 changes such that a replenishment operation is no longer permitted. For example, if, during a fluid replenishment cycle, the operator wishes to initiate an injection of fluid from the syringe, injector head 104 may terminate the fluid replenishment cycle and begin an injection procedure for injection of fluid from the syringe. Additional examples and embodiments pertaining to automated fluid replenishment operations will be further described in more detail below.

Figure 1B:
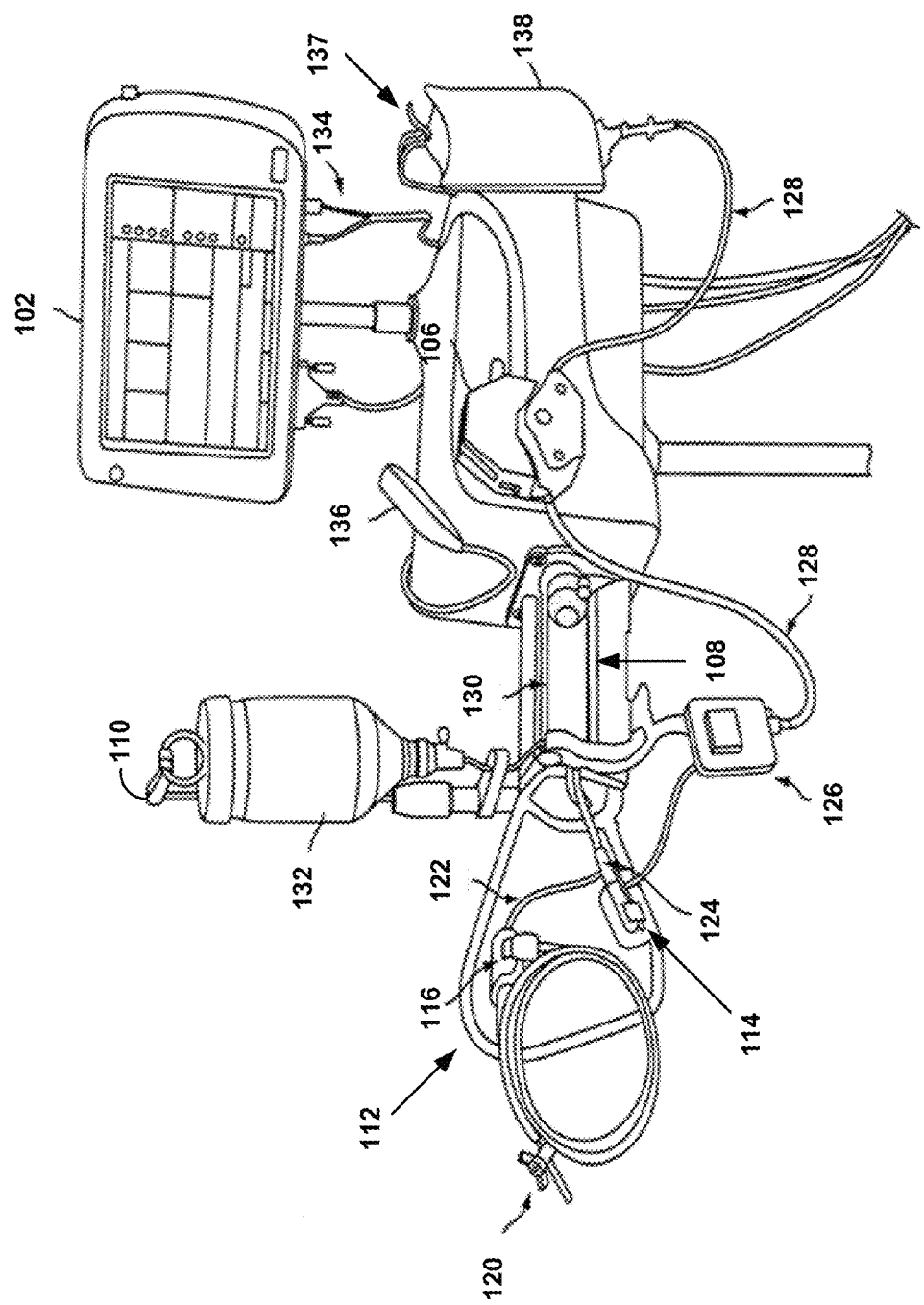
FIG. 1B is a perspective diagram of one embodiment of the powered medical fluid injection device of FIG. 1A connected to various components, including fluid reservoirs and tubing.

FIG. 1B is a perspective diagram of one embodiment of the powered medical fluid injection device 100 of FIG. 1A connected to various components, including fluid reservoirs and tubing. For example, FIG. 1B shows a first fluid reservoir 132 and a second fluid reservoir 138. First fluid reservoir 132 contains a first fluid, such as contrast media. An operator may hang first fluid reservoir 132 on reservoir holder 110. In some cases, first fluid reservoir 132 may be a glass reservoir, while in other cases, it may be a plastic reservoir. The fluid contained within first fluid reservoir 132 may be drawn through tubing and into a pressurizing unit 130 (e.g., a syringe) that has been inserted into sleeve 108 during operation. During an automatic replenishment operation, device 100 may automatically supply pressurizing unit 130 with an amount of fluid from first fluid reservoir 132.

Second fluid reservoir 138 may contain a second fluid, such as saline. An operator may hang second fluid reservoir 138 on a hook 137. In some cases, second fluid reservoir 138 may be a plastic reservoir, such as a bag. The fluid contained within second fluid reservoir 138 may be drawn through tubing 128 through operation of pump 106.

FIG. 1B also shows that a hand-control device 136 is coupled to control panel 102 via a connector 134. In one embodiment, hand-control device 136 may be connected to another component of device 100 other than control panel 102. As shown in FIG. 1B, hand-control device 136 is coupled to tubing, cabling, or wiring, which connects hand-control device 136 to connector 134. Connector 134 may then be connected to or disconnected from control panel 102. An operator may manipulate hand-control device 136 to control injection of fluid from device 100. For example, the operator may use hand-control device 136 as a variable-rate control device to variably control the rate of flow of fluid from device 100 (e.g., flow of fluid out of pressurizing unit 130). In one embodiment, hand-control device 136 may comprise an electrical device. In one embodiment, hand-control device 136 may comprise a pneumatic device.

Tubing 128 is coupled to a pressure transducer 126. Pressure transducer 126 is also coupled to output, high-pressure tubing 122, which may be connected to a patient line via connector 120. When high-pressure tubing 122 is connected to a patient line (within a patient), pressure transducer 126 is capable of functioning as a hemodynamic monitor for the patient. Pressure transducer 126 converts detected pressures into electrical signals that may be monitored or otherwise used by device 100 or another monitoring device. High-pressure tubing 122 also runs through air detector 116. Air detector 116 is capable of detecting the presence of air (e.g., air bubbles or columns) within fluid that may be flowing through high-pressure tubing 122.

FIG. 1B also shows a manifold valve 124. This manifold valve 124 is connected to high-pressure tubing 122, as well as patient manifold sensor 114. Manifold valve 124 is capable of controlling a flow of fluid from pressurizing unit 130 and/or through pump 106 to high-pressure tubing 122. For example, in one embodiment, when manifold valve 124 is in a first position, fluid may flow from pressurizing unit 130 to high-pressure tubing 122. When manifold valve 124, however, is in a second position, fluid may flow through pump 106, via tubing 128, to high-pressure tubing 122. In one embodiment, manifold valve 124 may allow fluid flow to high-pressure tubing 122 from only one of pressurizing unit 130 or pump 106 at a time.

Figure 2A:
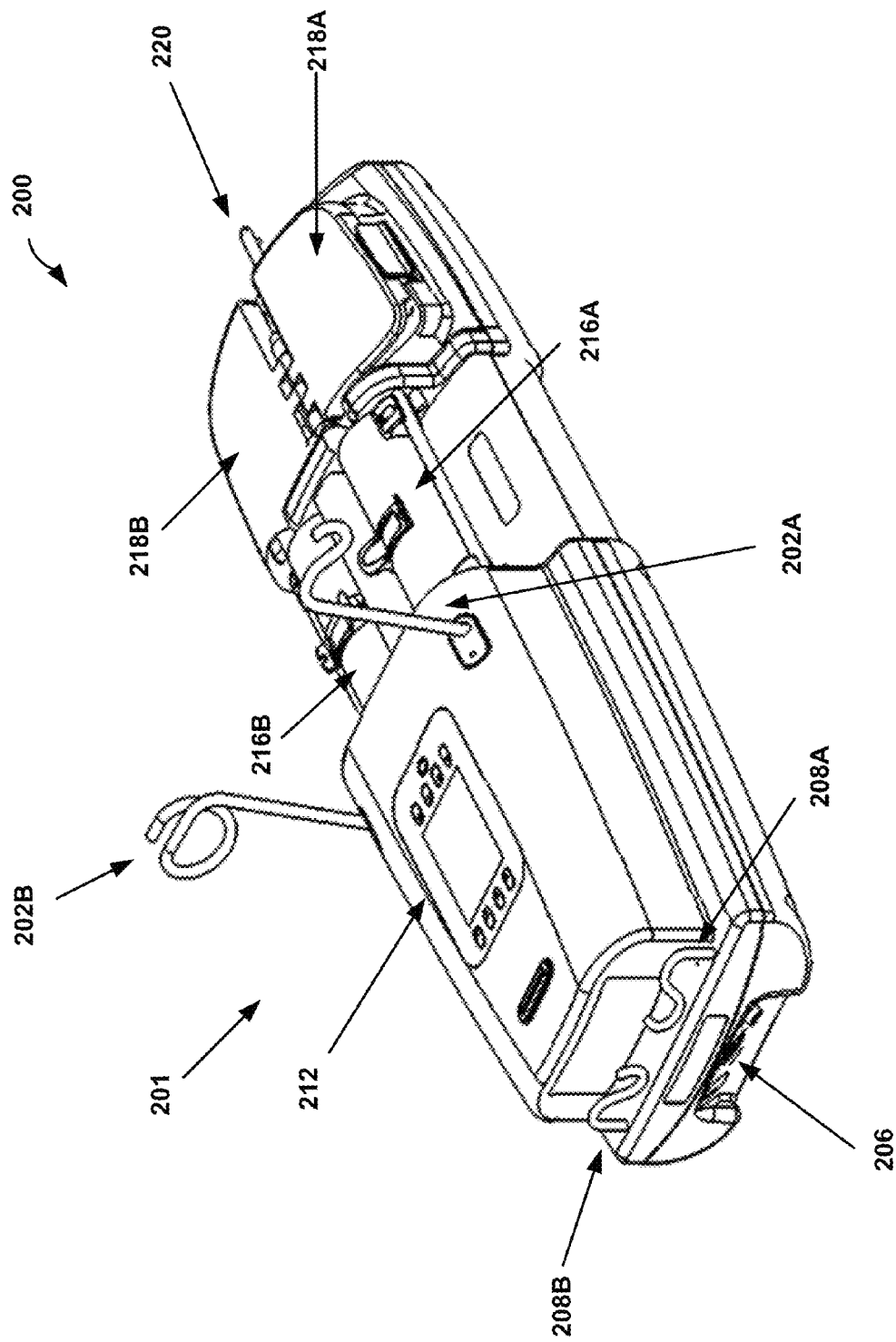
FIGS. 2A-2D are various perspective diagrams of another embodiment of a powered medical fluid injection device that may be used to automatically supply one or more pressurizing units with fluid.

FIG. 2A is a perspective diagram of another embodiment of a powered injection device 200 that may be used to perform various functions and, when operable, may initiate an automated fluid replenishment operation. In FIG. 2A, device 200 includes a first primary reservoir holder 202A, a second primary reservoir holder 202B, an electrical connection interface 206, a first backup reservoir holder 208A, a second backup reservoir holder 208B, a control panel 212, a first syringe sleeve 216A, a second syringe sleeve 216B, a first front-end assembly 218A, a second front-end assembly 218B, and a patient connection guide rod 220. In the embodiment of FIG. 2A, the pressurizing units that are used to deliver medical fluid are syringes that are contained within sleeves 216A and 216B. Injector head 201 includes reservoir holder 202A, reservoir holder 202B, connection interface 206, reservoir holder 208A, reservoir holder 208B, and control panel 212. Injector head 201 further includes one or more processors used to control and/or monitor the components of injector head 201 and other components of device 200.

Reservoir holder 202A is capable of holding a first reservoir of medical fluid, while reservoir holder 202B is capable of holding a second reservoir of medical fluid. In one embodiment, reservoir holder 202A holds a reservoir of a first type of fluid, such as contrast media, while reservoir holder 202B holds a reservoir of a second, different type of fluid, such as a diluent (e.g., saline). Different forms of reservoirs (e.g., bottles, bags) may be used with reservoir holders 202A and 202B. Because device 200 may be used to inject medical fluid over multiple patient procedures, the reservoirs held by holders 202A and 202B may need to be replaced over time. Typically, an operator of device 200 manually replaces the reservoirs on holders 202A and 202B. For operator convenience, device 200 additionally includes backup holders 208A and 208B. The operator may store backup fluid reservoirs on holders 208A and 208B. When a reservoir on primary holder 202A or 202B runs empty and needs to be replaced, operator may quickly and easily access a new fluid reservoir from one of backup holders 208A or 208B and attach to primary holder 202A or 202B.

Device 200 includes electrical connection interface 206 to directly or indirectly couple device 200 to an external medical device, such as a medical imaging device. Typically, device 200, when used as a contrast media injection device, works in conjunction with a medical imaging device. For example, device 200 may work in conjunction with a medical imaging device during an angiographic or CT procedure. Connection interface 206 is used to directly or indirectly connect device 200 to such an imaging device. In one embodiment, device 200 may transmit injection and/or control information to an external imaging device via interface 206, and may receive imaging and/or control information from the external imaging device via interface 206, as well.

FIG. 2A shows that device 200 also includes control panel 212. Control panel 212 is located on the top side of example device 200. The operator may interact with control panel 212 to program various injection procedure parameters and/or protocols that may be used for injection procedures. The operator may also use control panel to set up device 200 for use, to begin, pause, resume, or end a procedure, or to view various injection-related information (such as flow rate, volume, pressure, rise time, procedure type, fluid information, and/or patient information). FIG. 2A shows various user-activated buttons on the side of control panel 212. However, in one embodiment, control panel 212 may include a touch-activated screen.

In one embodiment, a separate, larger control panel (not shown) may also be in communication with device 200. In this embodiment, the larger control panel provides similar operator functionality to that provided by control panel 212. However, the larger control panel may be mounted to a rail of a bed on which a patient is lying, or may be mounted to other devices separate from device 200. In one embodiment, the larger control panel looks similar to control panel 102 shown in FIG. 1A.

Device 200 is a dual-syringe device that includes two syringes contained within sleeves 216A and 216B. Both syringes are capable of delivering medical fluid to a patient.

In one embodiment, the syringe within sleeve 216A is capable of drawing in fluid from a fluid reservoir coupled to holder 202A, and the syringe within sleeve 216B is capable of drawing in fluid from a fluid reservoir coupled to holder 202B. For example, these syringes may draw in fluid during a fluid replenishment operation. Each syringe is coupled to a motor/actuator assembly (not shown) that drives a plunger in one of two directions. During a fluid replenishment cycle, for example, a motor/actuator assembly of device 200 may drive a plunger within the syringe in sleeve 216A in one direction to draw fluid from a reservoir coupled to holder 202A into the syringe. During an injection cycle, the motor/actuator assembly of device 200 may drive the plunger within this syringe in the opposite direction to expel fluid. In one embodiment, device 200 contains two distinct motor/actuator assemblies, such that one assembly drives the syringe within sleeve 216A while another drives the syringe within sleeve 216B. These motor/actuator assemblies are part of injector head 201, and may individually be controlled or monitored by the one or more processors included within injector head 201.

Fluid input tubing couples the syringes within sleeves 216A and 216B to the fluid reservoirs and to output lines, according to one embodiment. In one embodiment, the syringes each are dual-port syringes (such as the dual-port syringe shown in FIG. 3). In this embodiment, one syringe port is used for input tubing that is coupled to a fluid reservoir, while the second port is used for output tubing that is operatively coupled to an output (patient) line through assemblies 218A or 218B.

Front-end assembly 218A is associated with sleeve 216A, and front-end assembly 218B is associated with sleeve 216B. Output tubing from the syringe in sleeve 216A runs through assembly 218A and out to a patient line, while output tubing from the syringe in sleeve 216B runs through assembly 218B and out to the patient line. Each assembly 218A and 218B includes a door, or cover, which may be opened and closed by the operator. For the example, the operator may open the door when loading tubing and may be closed upon loading. In one embodiment, each door may be made of a transparent or translucent material, such that the operator may see inside the contents of the assembly 218A or 218B even when the door is closed.

In one embodiment, each front-end assembly 218A and 218B includes air detectors and valve components (not shown). Air detectors are used to detect air bubbles or air columns within the fluid tubing that is used. The valve components are used to allow or restrict fluid flow through tubing. For example, when pinch valves are used, the valves pinch fluid tubing to restrict fluid flow in one state, but stay open to allow fluid flow in another state. Various different forms of valves may be used within assemblies 218A and 218B. In addition, various different forms of air detectors (e.g., ultrasonic, optical) may be used, as well.

In one embodiment, the input and output tubing that is coupled to the syringe in sleeve 216A runs through front-end assembly 218A, and the input and output tubing that is coupled to the syringe in sleeve 216B runs through front-end assembly 218B. In this embodiment, each assembly 218A and 218B contains a first pinch valve and a first air detector coupled to the input tubing for the respective syringe, and further contains a second pinch valve and a second air detector coupled to the output tubing for the respective syringe. These components are more clearly shown in FIG. 2D and will be discussed in more detail below.

Figure 4:
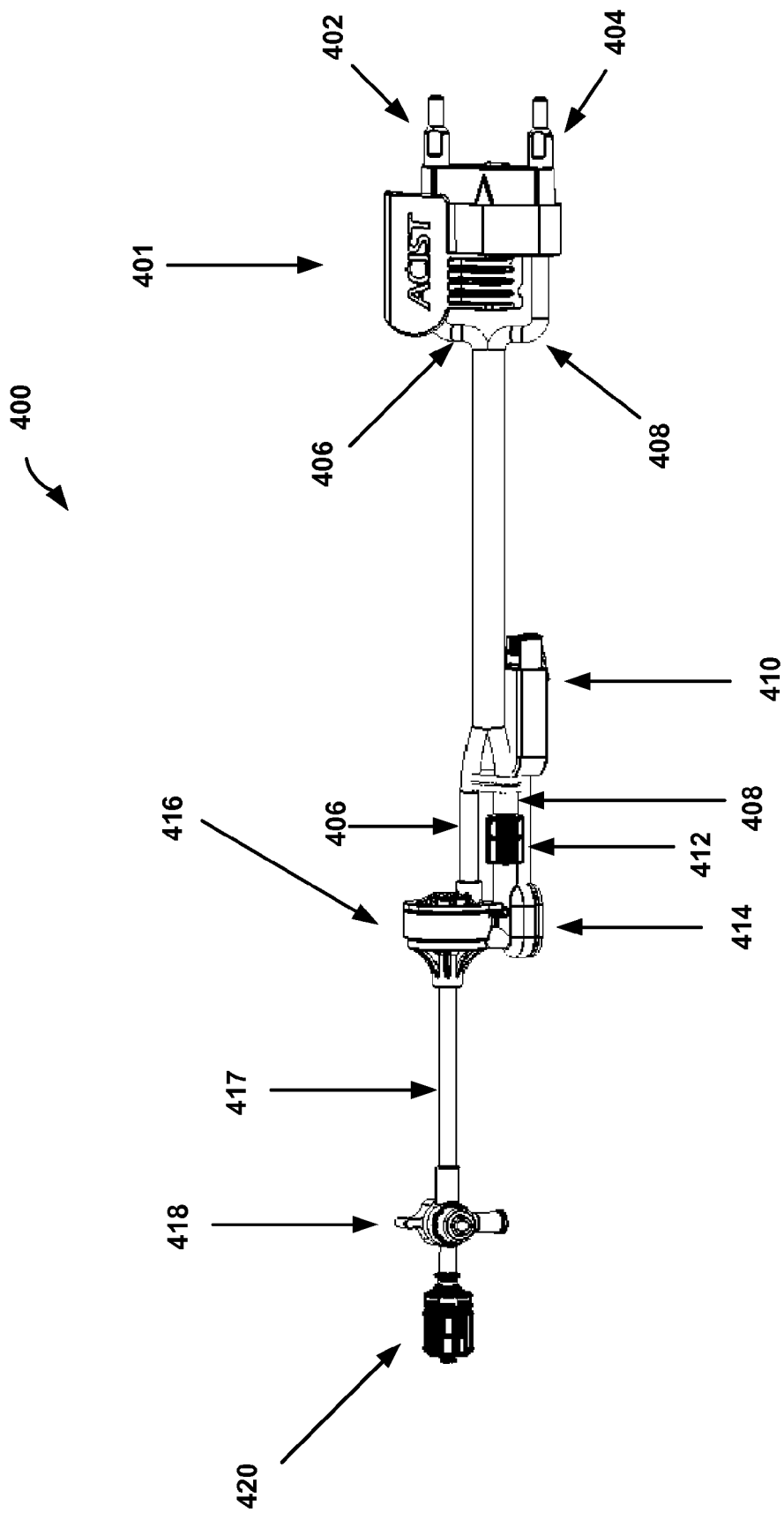
FIG. 4 is a perspective diagram of a patient line that may be used with a powered medical fluid injection device, according to one embodiment.

FIG. 2A also shows a patient connection guide rod 220. The output tubing from syringes 216A and 216B run through front-end assemblies 218A and 218B, respectively, and are then coupled to a patient line, or kit (not shown). The patient line is a single-use line, according to one embodiment, that is used for a single patient procedure. Each patient line may be connected to and disconnected from the output tubing running through front-end assemblies 218A and 218B. The patient line is connected to the output tubing via connection guide rod 220, according to one embodiment. The patient line may slide over connection guide rod 220 in order to become coupled with the output tubing. In one embodiment, the patient line includes two tubing elements, each element corresponding to one of the output tubing elements of the syringe in sleeve 216A or 216B. An example patient line is shown in FIG. 4 and will be discussed in more detail below.

In one embodiment, a medical fluid injection device, such as device 200, may include a plurality of pressurizing units, including three or more pressurizing units. Each of these pressurizing units may be included within a separate sleeve during operation. In some cases, multiple pressurizing units may contain the same type of fluid. For example, a first pressurizing unit may contain contrast media, a second pressurizing unit may contain a diluent (e.g., saline), and a third pressurizing unit may contain contrast media. In this scenario, the third pressurizing unit may comprise a backup, or secondary, source of contrast media. In this example, the first and third pressurizing units may both be coupled to a common front-end assembly, such as a front-end assembly similar to 218A or 218B.

Figure 2B:
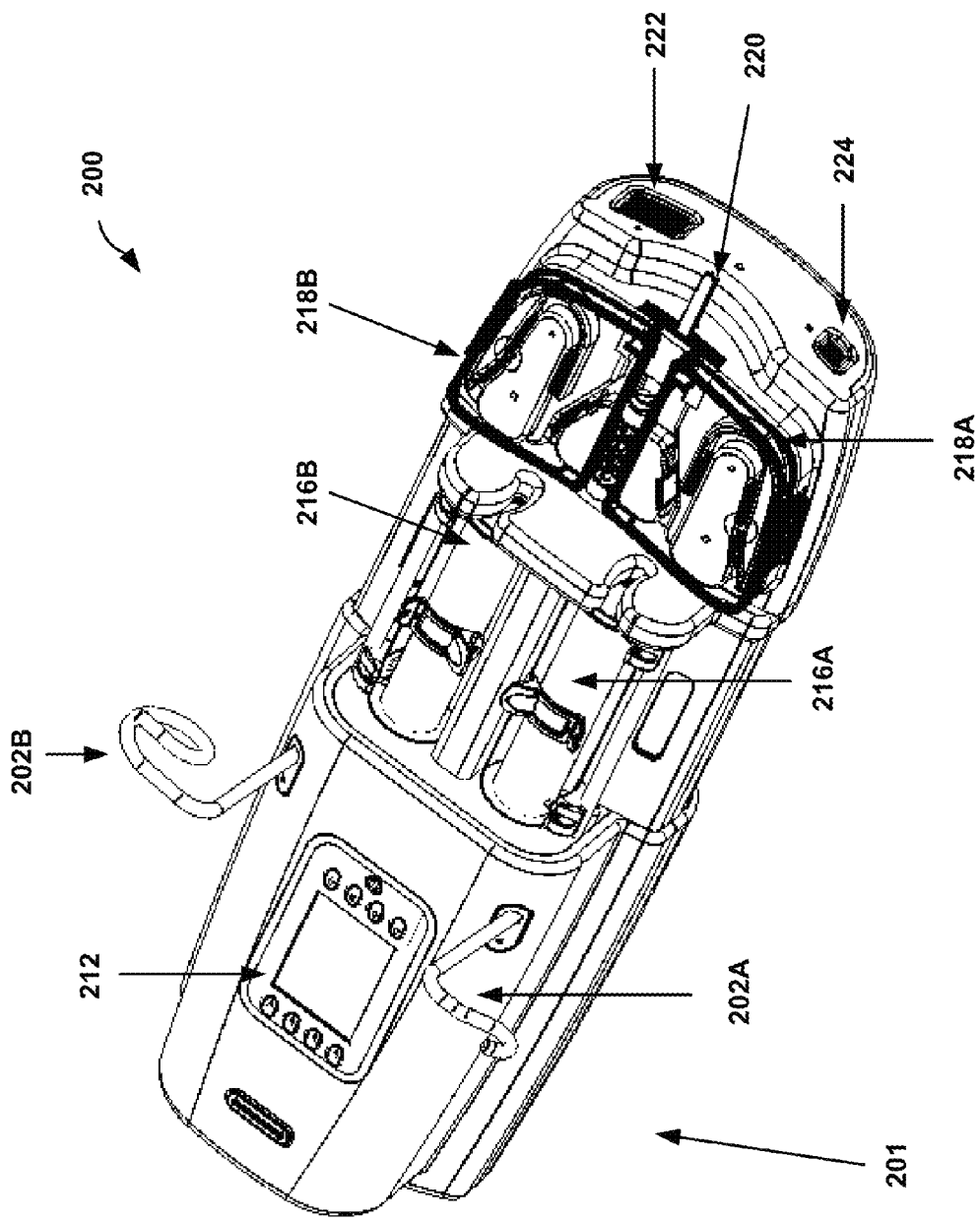

FIG. 2B is another perspective diagram of device 200 shown in FIG. 2A. In FIG. 2B, sleeves 216A and 216B, along with front-end assemblies 218A and 218B, can be more clearly seen. Although the doors of assemblies 218A and 218B are closed in the example of FIG. 2B, they are made of a semi-transparent material, such that the interior pinch valve and air detector components may be more clearly seen. FIG. 2B also shows connection ports 222 and 224. In one embodiment, a pressure transducer connector (such as one coupled to connector 410 shown in FIG. 4), may be connected to connection port 224. The pressure transducer connector is operatively coupled to a pressure transducer, which measures patient hemodynamic signals on the patient line. By connecting a pressure transducer to connection port 224, device 200 is capable of utilizing and processing hemodynamic pressure signals of a patient that are detected in the patient line.

Device 200 also includes connection port 222, which may be connected to a hand-control device (not shown). In one embodiment, the hand-control device is a disposable component that may be used by the operator for a single patient procedure. The hand-control device may control the operation of one or both of syringes in sleeves 216A and 216B. For example, the operator may push a button or otherwise interact with the hand-control device to cause a motor/actuator assembly to inject fluid from the syringe in sleeve 216A, and may push another button or otherwise interact with the hand-control device to cause a motor/actuator assembly to inject fluid from the syringe in sleeve 216B. Thus, if the syringe in sleeve 216A contains contrast media, and the syringe in sleeve 216B contains a diluent, the operator may push one button on the hand-control device to inject contrast into the patient line, and may push another button to inject saline. In one embodiment, the hand-control device contains variable-rate functionality, such that the harder the operator pushes on a button or actuates a component, the greater the flow rate of injected fluid from the syringe in sleeve 216A or 216B.

Figure 2C:
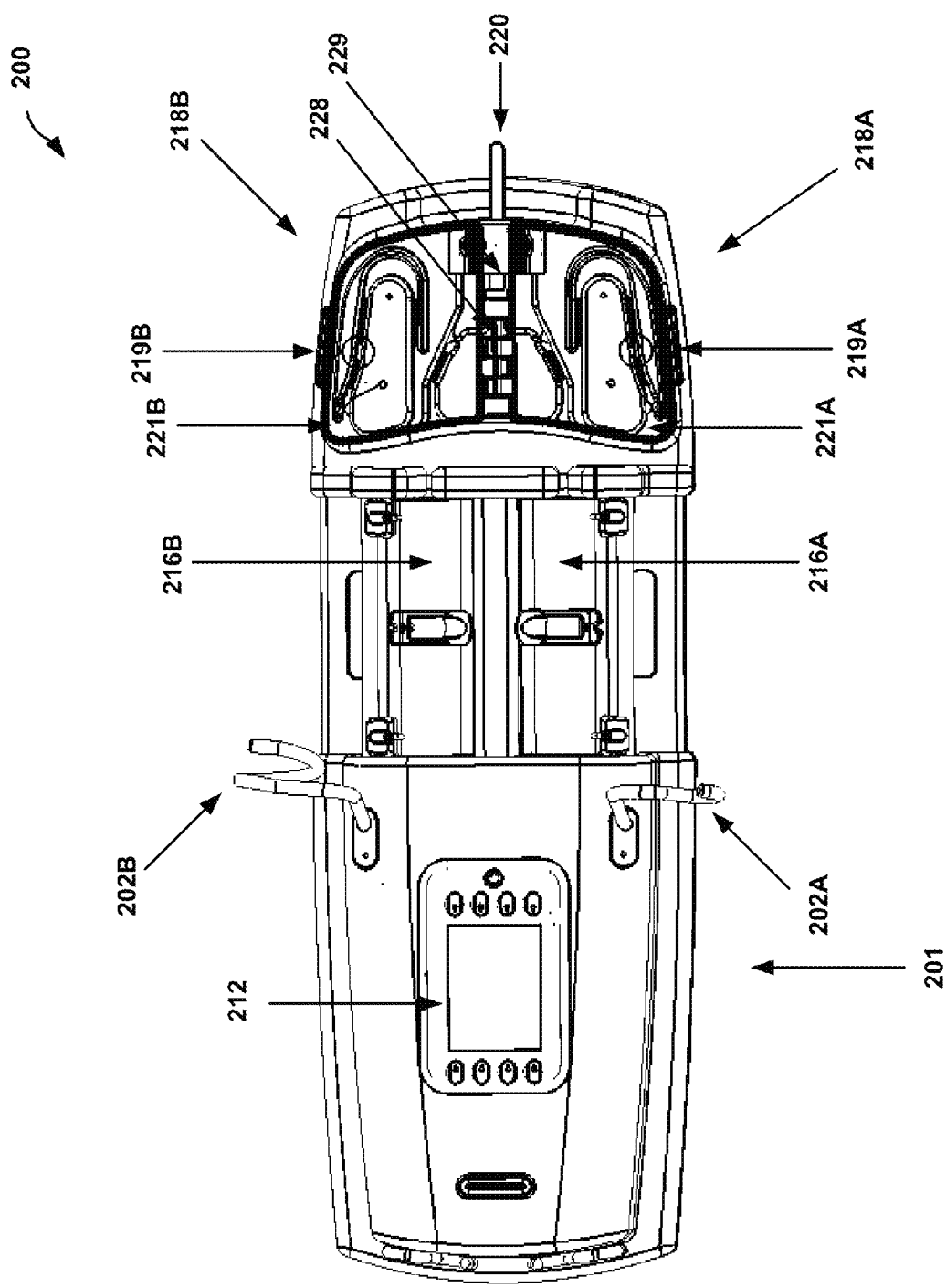

FIG. 2C is another perspective diagram of device 200. FIG. 2C shows a top view of device 200, according to one embodiment.

FIG. 2C also shows doors 221A and 221B on front-end assemblies 218A and 218B, respectively. As noted above, in one embodiment, each of assemblies 218A and 218B include a moveable door 221A and 221B, respectively. Door 221A covers assembly 218A, and door 221B covers assembly 218B. In the embodiment of FIG. 2C, doors 221A and 221B are made of a transparent, or semi-transparent, material, such that an operator may see the contents of assemblies 218A and 218B (which are shown in more detail in FIG. 2D). Door 221A includes a handle 219A, and door 221B includes a handle 219B. The operator may utilize handles 219A and 219B to open and close doors 221A and 221B, respectively. Doors 221A and 221B are coupled to one or more hinges 228, which allow doors 221A and 221B to be opened and closed.

Also shown in FIG. 2C is a pivot pin 229. Pivot pin 229 is inserted through hinges 228, according to one embodiment, to securely allow doors 221A and 221B to be freely opened and closed by an operator. Doors 221A and 221B pivot about an axis that runs through pivot pin 229.

In one embodiment, pivot pin 229 is screwed into place. Pivot pin 229 may also be removed by an operator. For example, the operator may unscrew pivot pin 229 and remove it from front-end assemblies 218A and 218B. After pivot pin 229 has been removed, doors 221A and 221B may also be removed from assemblies 218A and 218B. For example, the operator may choose to remove doors 221A and 221B if the operator wishes to clean or replace doors 221A and 221B.

Figure 2D:
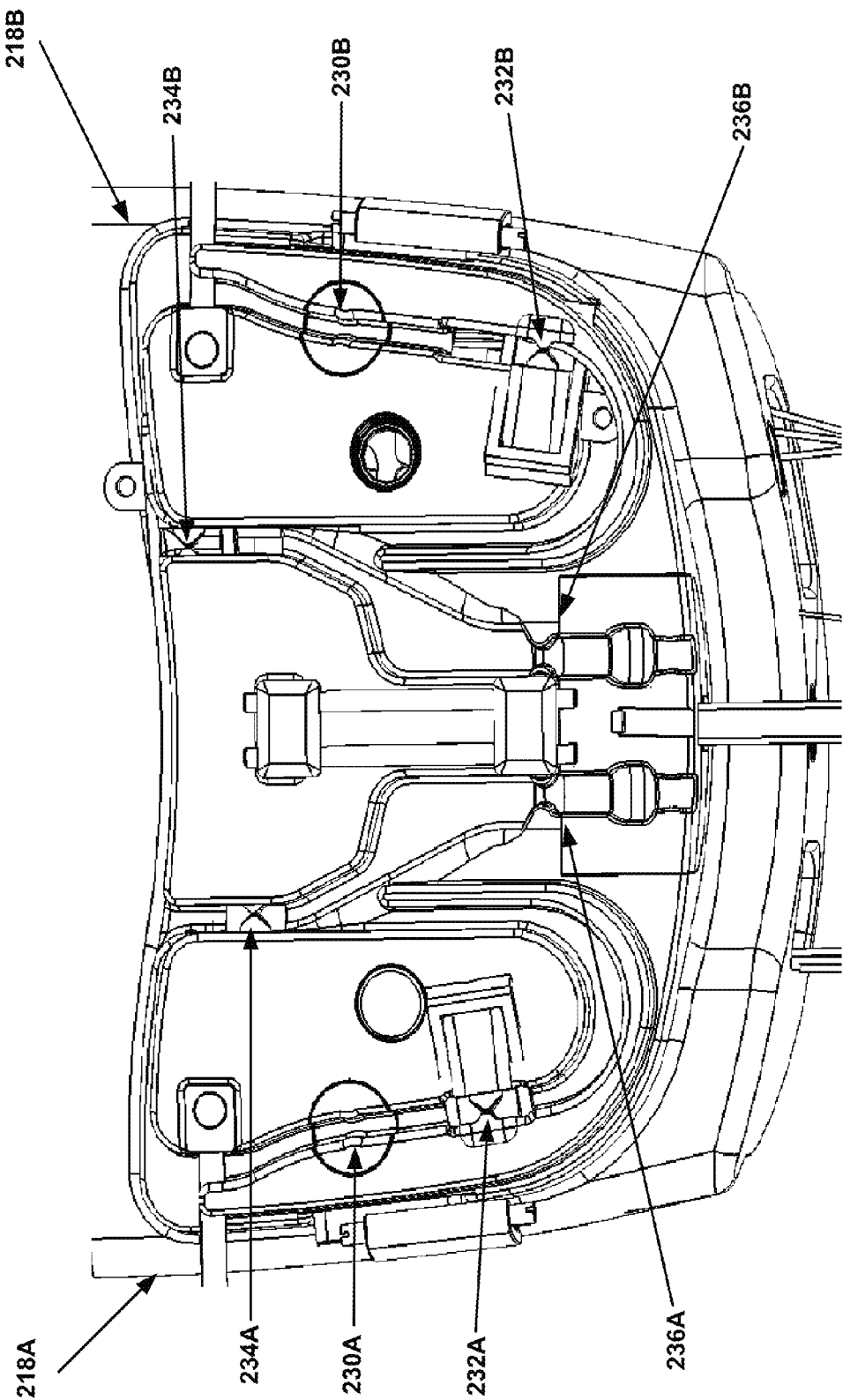

FIG. 2D is a perspective view of front-end assemblies 218A and 218B shown in more detail, according to one embodiment. Although doors 221A and 221B are not shown in FIG. 2D, they are made of a transparent, or semi-transparent, material, such that the contents of assemblies 218A and 218B may be more clearly seen by an operator, even when doors 221A and 221B are closed.

Front-end assembly 218A includes a first air detector 230A, a first pinch valve 232A, a second pinch valve 234A, and a second air detector 236A. Input tubing from a reservoir on holder 202A runs through air detector 230A and pinch valve 232A and into a syringe in sleeve 216A via a first syringe port, according to one embodiment. Output tubing coupled to a second syringe port of the syringe in sleeve 216A runs through pinch valve 234A and air detector 236A and is then coupled an external patient line, or kit (such as the one shown in FIG. 4). Air detector 230A is used to detect air bubbles or columns within the input tubing, and air detector 236A is used to detect air bubbles or columns within the output tubing. Air detectors 230A and 236A may comprise acoustic-based, optical-based, or other forms of air detectors. If either or both of air detectors 230A and 236A detect a measurable amount of air in the input and/or output tubing, these detectors may propagate signals to injector head 201 of device 200. One or more processors of injector head 201 may process these received signals. Injector head 201 may provide a warning message or alert to the operator via control panel 212, such that the operator may take appropriate action. Injector head 201 may also, in one embodiment, automatically pause or terminate any injection of fluid from the syringe in sleeve 216A if air has been detected in the input and/or output tubing, by controlling operation of the motor/actuator assembly driving the syringe.

Pinch valve 232A controls a flow of fluid from input tubing into the syringe in sleeve 216A. Injector head 201 controls the operation of pinch valve 232A. When injector head 201 opens pinch valve 232A, fluid may flow from the reservoir connected to holder 202A and into the syringe. When pinch valve 232A is closed, no fluid flow is permitted within the input tubing. For example, when injector head 201 is supplying the syringe with fluid, it may open pinch valve 232A to allow fluid flow in the input tubing, but it may also close pinch valve 234A, to prohibit any fluid flow in the output tubing. The plunger within the syringe may be moved in a first direction (by the motor/actuator assembly) to supply fluid to the syringe. When a fluid injection occurs, the motor/actuator assembly will move the plunger within the syringe in a second, opposite direction. Injector head 201 may close pinch valve 232A during an injection procedure, to prohibit fluid flow in the input tubing. However, injector head 201 may open pinch valve 234A, to allow fluid flow in the output tubing during such a procedure. In such fashion, injector head 201 utilizes pinch valves 232A and 234A to control fluid flow in the input and output tubing during various operations (e.g., replenishment and injection operations).

In one embodiment, pinch valves 232A and 234A are solenoid-based pinch valves. In other embodiments, other forms of pinch valves 232A and 234A may be used, such as pneumatic-based valves. In one embodiment, pinch valves 232A and 234A have default states in the closed position. Thus, when device 200 is neither supplying fluid into nor injecting fluid from the syringe in sleeve 216A, both pinch valves 232A and 234A are closed. Pinch valves 232A and 234A may then be opened by device 200 when energy is actively applied to pinch valves 232A and/or 234A. When no energy is applied to pinch valves 232A and/or 234A, they return to a default, closed position. Thus, if there are any power failures to device 200, valves 232A and 234A will return to closed position. This may help improve the safety of device 200.

Similarly, front-end assembly 218B includes a first air detector 230B, a first pinch valve 232B, a second pinch valve 234B, and a second air detector 236B. Input tubing from a reservoir connected to holder 202B runs through air detector 230B and pinch valve 232B and into a first syringe port of the syringe in sleeve 216B. Output tubing coupled to a second syringe port of the syringe runs through pinch valve 234B and air detector 236B, and may then be coupled to a patient line. The components within device 218B function similarly to those contained within device 218A as described above, according to one embodiment.

In one embodiment, device 200 of FIGS. 2A-2D is capable of initiating fluid replenishment cycles for the syringes in sleeves 216A and/or 216B during different operational states of device 200. In this embodiment, injector head 201 may obtain operational state information for the device, such as, for example, the type of operational state information described with reference to FIGS. 1A-1B. Injector head 201 then is capable of using the operational state information to determine whether it will permit a fluid replenishment operation for one or both of the syringes. If a fluid replenishment operation is permitted for one of these syringes, injector head 201 then initiates a fluid replenishment operation with a determined amount of medical fluid. The operational state information includes information other than a fluid delivery volume for a subsequent injection procedure, according to one embodiment, such that device 200 need not necessarily need to know an amount of fluid that is to be injected from the syringe in sleeve 216A or 216B for a patient injection procedure in order to determine whether or not to allow and initiate a fluid replenishment operation. This may provide a more effective and efficient way by which to supply the syringes with fluid.

For example, injector head 201 may obtain operational state information at a given point in time to determine that device 200 is injecting fluid from the syringe in sleeve 216A, but is not injecting fluid from the syringe in sleeve 216B. Given this operational state information, injector head 201 may then be able to determine that it can supply the syringe in sleeve 216B with fluid, if necessary, given that this syringe is not currently being used to inject fluid. Injector head 201 may first check to see if this syringe is already full, such as by checking additional operational state information or by making a calculation. If the syringe is already full, injector head 201 need not initiate a fluid replenishment operation, since it determines that a supply amount would essentially be equal to zero. If, however, the syringe is not full to capacity, injector head 201 may supply the syringe in sleeve 216B with a determined amount of fluid. For example, injector head 201 may cause the syringe to be completely filled to capacity. Or, injector head 201 may otherwise use operational state information to determine an amount of fluid to use during the fluid replenishment operation.

Injector head 201 may determine whether the syringe in sleeve 216B is already full using a number of different approaches. For example, in one scenario, injector head 201 may use operational state information to determine how much fluid remains in the syringe. In another scenario, injector head 201 may calculate an amount of remaining fluid based upon an amount of fluid that has been injected from the syringe in prior injection procedures, which may also be obtained from operational state information of device 200. Operational state information includes current and past state information about device 200, including operational information, injection parameters used, error messages, alert conditions, and any other related information.

Using another example, injector head 201 may also gather operational state information indicating that neither of the syringes in sleeves 216A or 216B is being used to inject fluid at a given time. This may be the case when an operator is using control panel 212 to set up injection parameters for one or more subsequent procedures to be performed. In this case, injector head 201 may initiate a fluid replenishment operation for both of the syringes.

When injector head 201 is supplying the syringe in sleeve 216A or 216B with fluid, it continually monitors the state of device 200, according to one embodiment. If the state of device 200 changes, injector head 201 may pause or abort a fluid replenishment operation that is taking place. For example, if device 200 is automatically supplying the syringe in sleeve 216A with fluid, but detects that the operator now wants to initiate an injection procedure using fluid from this syringe, injector head 201 will stop the fluid replenishment operation and initiate an injection operation. During any of these operations, injector head 201 may utilize one or more of its processors to perform certain operations.

In one embodiment, a fluid replenishment operation may be permitted if at least a determined amount of time has elapsed since a prior injection of medical fluid from one of the pressurizing units (e.g., syringes) in sleeve 216A or 216B. For example, when a syringe delivers fluid to a catheter in a patient, a clinician may inject intermittent, frequent "puffs" of contrast media from device 200 during placement of the catheter within the patient. In this example, it may sometimes be beneficial to avoid, or prohibit, replenishment operations in between these "puff" injections. Thus, a fluid replenishment operation may, in some cases, only be permitted if a determined amount of time (e.g., 30 seconds) has elapsed since a prior injection, or "puff," of contrast media. In some cases, a fluid replenishment operation may be permitted if a fluid volume in the syringe has decreased at least a determined amount since a prior replenishment operation was performed.

Table 1 below shows examples of a number of different states of operation of device 200 during which one or more fluid replenishment operations of the syringes in sleeves 216A and 216B may be initiated. From the examples shown in Table 1, it is assumed that the syringe in sleeve 216A is used for injecting contrast media and that the syringe in sleeve 216B is used for injecting saline, which is a diluent. Additional states and/or operations to those listed may also be possible.

TABLE 1

| STATE OF INJECTION DEVICE 200 | FLUID REPLENISHMENT OPERATION |
|---|---|
| Contrast media purge from syringe in sleeve 216A | Supply saline to syringe in sleeve 216B |
| Saline purge from syringe in sleeve 216B | Supply contrast media to syringe in sleeve 216A |
| Contrast media injection from syringe in sleeve 216A | Supply saline to syringe in sleeve 216B |
| Saline injection (or KVO cycle) from syringe in sleeve 216B | Supply contrast media to syringe in sleeve 216A |
| Injection parameter entry/change by operator on control panel 212 | Supply contrast media to syringe in sleeve 216A and/or supply saline to syringe in sleeve 216B |
| Standby mode for device 200 | Supply contrast media to syringe in sleeve 216A and/or supply saline to syringe in sleeve 216B |
| Contrast media reservoir change by operator (such as by replacing reservoir on holder 202A) | Supply saline to syringe in sleeve 216B |
| Saline reservoir change by operator (such as by replacing reservoir on holder 202B) | Supply contrast media to syringe in sleeve 216A |

In the examples of Table 1, purge operations from the syringes in sleeves 216A and/or 216B occur when device 200 is being primed, or prepared, for patient use. Thus, during purge operations, device 200 is not yet connected to a patient. Conversely, during injection operations from the syringes, fluids are injected into a patient. Device 200 may also be used for KVO, or "keep vessel open", operations. A KVO operation occurs when small amounts of diluent are repeatedly or continuously injected. Also in reference to Table 1, device 200 may be in standby mode when neither syringe is being used to inject fluid. For example, device 200 may enter standby mode after a patient case has been finished, and before the operator has entered parameters or otherwise configured the device using panel 212 for a new case. In one embodiment, the examples shown in Table 1 are based upon an assumption that only one of the contrast media or diluent is injected at a time.

In some cases, during an automatic fluid replenishment operation, a user or operator may intervene by interacting with the control panel, such as control panel 102 (FIG. 1A) or control panel 212. For instance, an operator may choose to terminate a fluid replenishment operation, or may choose to modify one or more fluid supply parameters.

FIG. 3 is a perspective diagram of an example syringe 301 that may be used within device 200, according to one embodiment. Syringe 301 may be loaded in either sleeve 216A or 216B. If syringe 301 is loaded into sleeve 216A, it may be coupled to a fluid reservoir connected to holder 202A (FIG. 2A), and may further be coupled to a patient line (FIG. 4).

Syringe 301 is a dual-port syringe in the example of FIG. 3. Input port 300 is coupled to input tubing 308, and output port 302 is coupled to output tubing 304. Input tubing is coupled to a connector 310, which may be connected to a fluid reservoir in holder 202A, assuming syringe 301 is loaded into sleeve 216A. For example, if connector 310 is a spike, the spike may be inserted into a bottle of medical fluid connected to holder 202A. Output tubing 304 is coupled to a connector 306, which couples output tubing 304 to a separate patient line. In one embodiment, connector 306 is a Luer-type connector.

Fluid is drawn from the fluid reservoir into port 300 of syringe 301 via input tubing 308. Fluid is expelled from port 302 of syringe 301 into output tubing 304. Input tubing 308 may run through air detector 230A and pinch valve 232A (FIG. 2D) of front-end assembly 218A, which was described in more detail above, while output tubing 304 may run through pinch valve 234A and air detector 236A. In one embodiment, syringe 301, along with input tubing 308, connector 310, output tubing 304, and connector 306, are disposable, multi-use components. That is, these components may be used within device 200 over multiple uses or patient procedures before they are disconnected from device 200 and disposed of. In another embodiment, these components are disposable, single-use components, meaning that they are disposed of after a single patient procedure.

In one embodiment, syringe 301 may also be used in device 100 (FIG. 1A). When used in device 100, connector 310 would be connected to a fluid reservoir on holder 110, and output tubing 304 would run through patient manifold sensor 114.

FIG. 4 is a perspective diagram of a patient line 400 that may be used with injection device 200 shown in FIGS. 2A-2C, according to one embodiment. Patient line 400 includes an assembly 401, a valve 416, a stopcock 418, and a connector 420. Patient line 400 is used to couple device 200 with a catheter that is used to deliver medical fluid to a patient.

Assembly 401 includes a first connector 402 and a second connector 404. When assembly 401 is coupled to device 200, connector 402 is connected with a connector for output tubing that is coupled to one of the syringes in sleeves 216A or 216B, while connector 404 is connected with a connector for output tubing that is coupled to the other syringe. For example, connector 402 may be connected to connector 306 (FIG. 3), which is coupled to output tubing 304 for the syringe in sleeve 216A. Patient line 400 is a disposable kit, in one embodiment, such that connectors 402 and 404 may be connected to and removed from tubing connectors, such as connector 306, by the operator. In one embodiment, patient line 400 is a single-use disposable kit, such that it is connected to device 200 for one patient use, and then subsequently disconnected and discarded.

Connector 402 is operatively coupled to tubing 406, and connector 404 is operatively coupled to tubing 408. In one embodiment, connector 402 is coupled to the syringe in sleeve 216A, which contains contrast media, while connector 404 is coupled to the syringe in sleeve 216B, which contains a diluent such as saline. Thus, in this embodiment, contrast media is injected into tubing 406 of patient line 400, while diluent is injected into tubing 408. Tubing 406 and 408 are coupled to valve 416, which, in one embodiment, comprises an elastomeric-type valve that allows fluid flow from only one of tubing 406 and 408 to output tubing 417. In one embodiment, valve 416 comprises a one-way valve that allows fluid flow only in the direction towards output tubing 417. Guide rod 220 may help, in some cases, maintain the sterility of connectors 402 and 404 by aligning these connectors, during insertion, to prevent contact with non-sterile items.

As is shown in FIG. 4, tubing 408 is coupled to check valve 412 and transducer 414. In one embodiment, check valve 412 comprises a bi-directional check valve. Transducer 414 comprises a pressure transducer in one embodiment that is capable of measuring hemodynamic signals of a patient when patient line 400 is coupled a catheter that has been inserted into the patient. Transducer connector 410 may be coupled to device 200, such as by way of port 224 (FIG. 2B). When connected, hemodynamic signals generated by transducer 414 may be processed by a processor within device 200.

Output tubing 417 is coupled to stopcock 418 and to connector 420 shown in FIG. 4. Stopcock 418 may be manually manipulated by the operator to control fluid flow, and may also be connected to other external devices, such as a syringe. Connector 420 is used to connect patient line 400 to an external catheter that may deliver fluid to a patient. In one embodiment, connector 420 comprises a Luer-type connector.

In one embodiment, patient line 400 may also be used with device 100 shown in FIG. 1A. When used with device 100, transducer connector 410 is coupled to a mating port within device 100 (not shown), such that a processor of device 100 may process the hemodynamic signals. Assembly 401 may also be coupled in device 100 in this embodiment. Patient line 400 may be coupled to a manifold valve that is coupled to patient manifold sensor 114, such that connection port 402 may be coupled to tubing from the syringe, while connection port 404 may be coupled to tubing running through pump 106. In this embodiment, tubing 417 may also be coupled to, or run through, air detector 116 of device 100.

Figure 5:
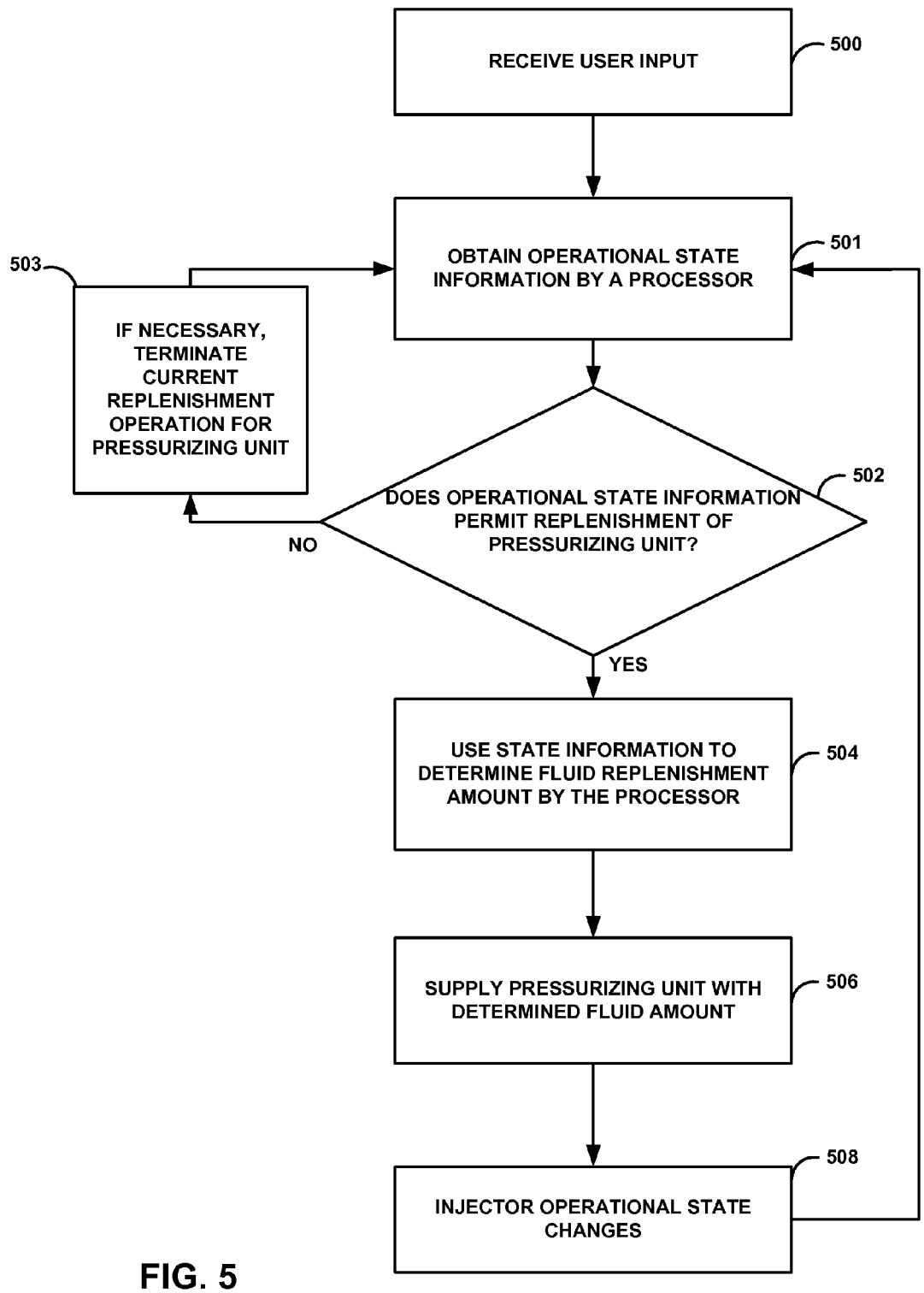
FIG. 5 is a flow diagram of a method that may be performed by a powered medical fluid injection device, according to one embodiment.

FIG. 5 is a flow diagram of an example method that may be performed by device 100 (FIG. 1A) or by device 200 (FIG. 2A), according to one embodiment, to initiate an automatic fluid replenishment operation. The method includes acts 500, 501, 503, 504, 506, and 508, and also includes checkpoint 502.

At 500, device 100 or device 200 may obtain user input. For example, a user or operator of device 100 may specify one or more parameters by interacting with control panel 102. A user may, for instance, arm or disarm device 100, provide one or more setup parameters, or turn on/off an auto supply mode. Typically, device 100 is capable of injecting fluid only when it is armed. Device 100 may, in one embodiment, perform automatic fluid replenishment operations when the auto supply mode is turned on.

At 501, device 100 or device 200 may obtain operational state information for the device. One or more processors of injector head 104 or injector head 201 may obtain this information. The operational state information may include current or prior state information, along with current or prior operational information for device 100 or device 200. At 502, device 100 or device 200 may determine whether the operational state information permits a fluid replenishment operation for one or more pressurizing units. For example, device 100 may determine whether such information permits a fluid replenishment operation of the syringe in sleeve 108, while device 200 may determine whether such information permits a fluid replenishment operation of syringe in sleeve 216A and/or 216B. In many cases, a fluid replenishment operation will be allowed if a given pressurizing unit is not currently being used to inject or purge any fluid.

If a fluid replenishment operation is not permitted (such as, for example, when the pressurizing unit is actively injecting or purging fluid), device 100 or 200 terminates, if necessary, any current fluid replenishment operation for the pressurizing unit at 503. For example, if device 200 is currently in the midst of a fluid replenishment operation of the syringe in sleeve 216A, but receives operational state information at 501 indicating that the operator wishes to proceed with an injection procedure using fluid from the syringe, device 200 will terminate the fluid replenishment operation. If, however, device 200 is not currently supplying the syringe in sleeve 216A with fluid, no additional action may need to be taken by device 200. Device 100 or 200 may then again obtain additional, new state information.

If, however, a fluid replenishment operation is permitted at checkpoint 502, device 100 or 200 uses the state information, at 504, to determine an amount of fluid (replenishment amount) to be supplied to the pressurizing unit. For example, one or more processors of injector head 104 or injector head 201 may determine whether the pressurizing unit (such as the syringe in sleeve 216A and/or 216B) is already full by using the state information. If it is full, the determined amount would be zero. If it is not full, device 100 or 200 may determine or calculate the amount based upon how much fluid has been injected from the pressurizing unit, or how much fluid is currently contained within the pressurizing unit.

At 506, device 100 or 200 supplies the pressurizing unit with the determined (supply) amount of fluid. Device 100 or 200 activates the motor/actuator assembly coupled to the pressurizing unit to initiate the fluid replenishment operation. A 508, the operational state of device 100 or 200 changes, thereby causing the device to repeat the method by obtaining new operational state information at 501 and again determining if a fluid replenishment operation is permitted at checkpoint 502. If, for example, device 100 or 200 had begun a replenishment operation, but new operational state information indicated that the pressurizing unit was now to be used for an injection, device 100 or 200 would end the fluid replenishment operation at 503.

Figure 6:
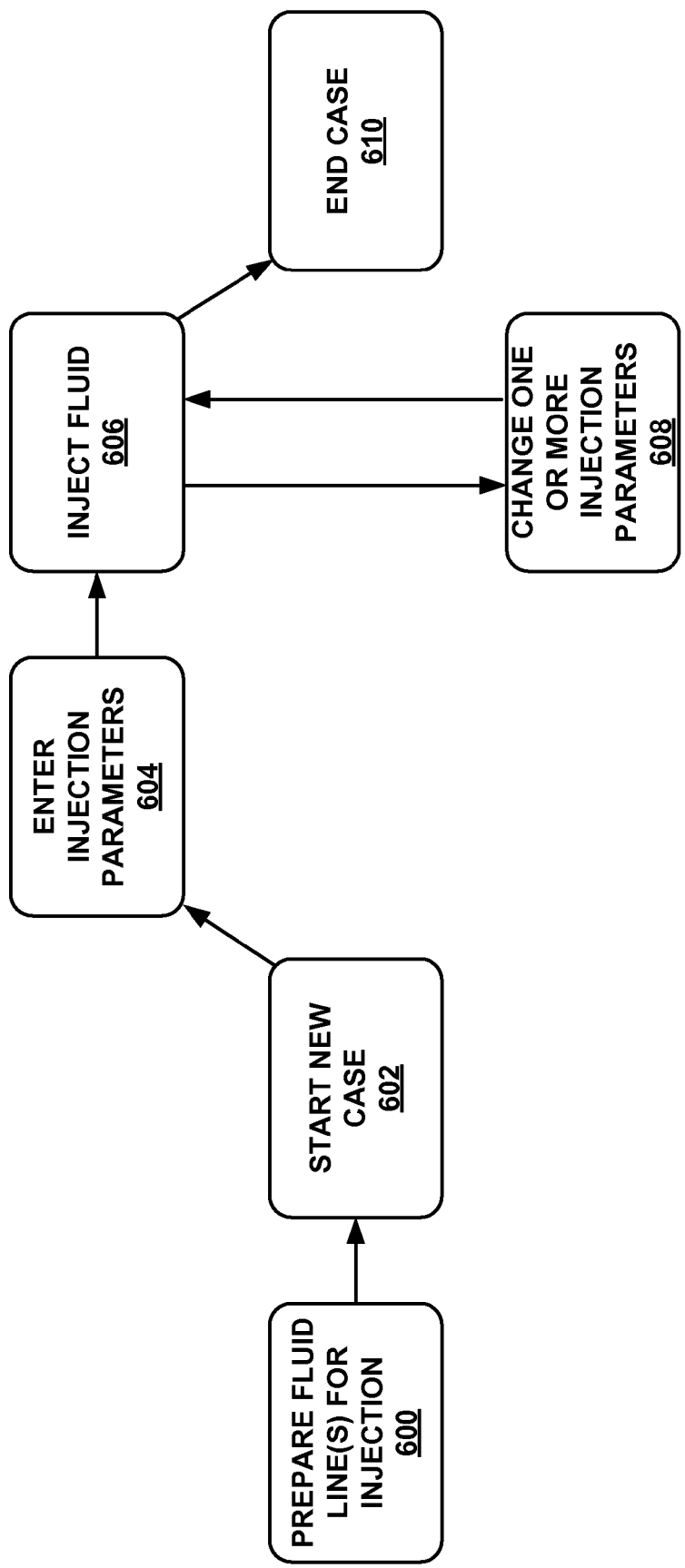
FIG. 6 is a conceptual diagram illustrating various operational states during which time a powered medical fluid injection device may initiate an automatic fluid replenishment operation for one or more pressurizing units.

FIG. 6 is a conceptual diagram illustrating various operational states during which time device 100 (FIG. 1A) or device 200 (FIG. 2A) may initiate a fluid replenishment operation for one or more pressurizing units. FIG. 6 shows example operational states 600, 602, 604, 606, 608, and 610. When obtaining any operational state information, device 100 or device 200 may utilize one or more processors, such as processors within injector head 104 or 201, to obtain information related to one or more of these operational states. For example, operational state information may include information about a current operational state for device 100 or 200, along with any other associated information. The example states shown in FIG. 6 provide examples of common operational states for device 100 or 200.

In state 600, device 100 or 200 prepares one or more fluid lines or pathways for injection. For example, in this state, device 100 or 200 may purge fluid tubing that is used with contrast media or with diluents in anticipation of later performing an injection procedure. If a given pressurizing unit is not be used during a given preparation function, it may be supplied with fluid. For example, if device 200 is preparing the fluid line for the output tubing coupled to the syringe in sleeve 216A during a purge cycle, injector head 201 may automatically supply the syringe in sleeve 216B with fluid.

In state 602, the operator may start a new case for device 100 or 200. For example, an operator may push a button or otherwise interact with control panel 102 (device 100) or control panel 212 (device 200) to start a new case. In this state, pressurizing units are not typically activated or being used. Thus, in state 602, device 100 has the opportunity to supply the syringe in sleeve 108 with fluid, while device 200 would has the opportunity to supply both syringes in sleeves 216A and 216B with fluid.

Similarly, in state 604, device 100 may supply the syringe in sleeve 108 with fluid, while device 200 may supply the syringes in sleeves 216A and 216B with fluid, given that the operator is entering injection parameters. Typically, the operator will enter these parameters using control panel 102 (device 100) or control panel 212 (device 200). Once the case has begun and the parameters have been entered, device 100 or 200 is ready to inject fluid.

In state 606, device 100 or 200 injects fluid using one or more pressurizing units. If a given pressurizing unit is not be used to inject fluid, it may potentially be supplied with fluid during a replenishment operation. Thus, for device 100, if fluid is being delivered only through pump 106, for example, device 100 may supply the syringe in sleeve 108 with fluid, assuming it is not already filled to capacity. In device 200, if a syringe in sleeve 216A is being used to deliver fluid, for example, device 200 may supply syringe in sleeve 216B with fluid, assuming it is not already filled to capacity. In some cases, an injection may be initiated manually be a user. In these cases, the user may manipulate a hand controller, such as hand controller 136 shown in FIG. 1B, to initiate an injection. In some cases, the injection may be initiated by an external system, such as an external X-ray system that is coupled to device 200.

During a case, the operator may choose to change one or more injection parameters. In state 608, the operator interacts with control panel 102 (device 100) or control panel 212 (device 200) to make such a change. Typically, no injections occur when the operator makes changes to injection parameters. Thus, in state 608, device 100 has the opportunity to supply the syringe in sleeve 108 with fluid, and device 200 has the opportunity to supply the syringes in sleeves 216A and 216B with fluid.

When a procedure is complete, the operator ends the case. Typically, the operator will interact with control panel 102 or control panel 212 to end the case. In state 610, when the case has ended, device 100 may take the opportunity to automatically supply the syringe in sleeve 108 with fluid, while device 200 may take the opportunity to automatically supply the syringes in sleeves 216A and 216B with fluid, given that no injection of fluid is taking place. Thus, as can be seen in the conceptual diagram of FIG. 6, there are multiple states during which device 100 or 200 has the opportunity to supply corresponding pressurizing units with fluid to improve or maximize the efficiency of these device.

Various embodiments have been described herein. These and other embodiments are within the scope of the following claims.

The invention claimed is:

1. A method comprising:
obtaining operational state information of a powered medical fluid injection device that is operatively coupled to a first pressurizing unit and also to a second pressurizing unit, the operational state information including information, other than a fluid delivery amount for a subsequent injection procedure, to describe an operating state or condition of the powered medical fluid injection device;
using the operational state information to determine whether the powered medical fluid injection device permits an automatic fluid replenishment operation for at least one of the first pressurizing unit and the second pressurizing unit; and
if the fluid replenishment operation is permitted for the first pressurizing unit, the method further comprises:
initiating the fluid replenishment operation in order to automatically supply the first pressurizing unit with medical fluid without any manual interaction by a user with the powered medical fluid injection device;
after initiation of the fluid replenishment operation, and while the first pressurizing unit is being supplied with the medical fluid, obtaining additional operational state information that is generated based on a manual interaction by the user with a control panel of the powered medical fluid injection device, wherein the additional operational state information specifies that the powered medical fluid injection device is to initiate a new injection procedure using the medical fluid of the first pressurizing unit;
after obtaining the additional operational state information, determine, based on the additional operational state information, that the powered medical fluid injection device will no longer permit the fluid replenishment operation for the first pressurizing unit;
upon determining that the fluid replenishment operation is no longer permitted, automatically terminating, without any manual interaction, the fluid replenishment operation for the first pressurizing unit; and
after terminating the fluid replenishment operation, initiating the new injection procedure, specified by the additional operational state information, using the medical fluid of the first pressurizing unit.

2. The method of claim 1, wherein the first pressurizing unit comprises a syringe, and wherein the medical fluid comprises at least one of a contrast medium and a diluent.

3. The method of claim 1, further comprising:
using the operational state information to determine an amount of the medical fluid to be supplied to the first pressurizing unit.

4. The method of claim 3, wherein using the operational state information to determine the amount of the medical fluid to be supplied to the first pressurizing unit comprises determining whether the first pressurizing unit is already filled to capacity.

5. The method of claim 4, wherein the determined amount of medical fluid is equal to zero when the first pressurizing unit is already filled to capacity.

6. The method of claim 1, wherein automatically supplying the first pressurizing unit with the amount of the medical fluid comprises filling the first pressurizing unit to capacity.

7. The method of claim 1, wherein automatically supplying the first pressurizing unit with the amount of the medical fluid comprises partially filling the first pressurizing unit.

8. The method of claim 1, wherein the fluid replenishment operation is no longer permitted for the first pressurizing unit if the additional operational state information indicates that the powered medical fluid injection device is delivering medical fluid from the first pressurizing unit.

9. The method of claim 1, wherein:
using the operational state information to determine whether the powered medical fluid injection device permits the fluid replenishment operation for the first pressurizing unit comprises determining whether the powered medical fluid injection device is delivering medical fluid from the second pressurizing unit.

10. The method of claim 9, further comprising:
if the powered medical fluid injection device is currently delivering medical fluid from the second pressurizing unit, determining that the fluid replenishment operation is permitted for the first pressurizing unit.

11. The method of claim 1, wherein automatically supplying the first pressurizing unit with the amount of medical fluid comprises supplying the first pressurizing unit with the medical fluid if the first pressurizing unit contains less than a specified amount of remaining fluid.

12. The method of claim 11, wherein the specified amount of remaining fluid comprises a threshold amount that is specified by a user-selectable parameter.

13. The method of claim 1, wherein using the operational state information to determine whether the powered medical fluid injection device permits the fluid replenishment operation for the first pressurizing unit comprises permitting the fluid replenishment operation if at least a determined amount of time has elapsed since a prior injection of medical fluid from the first pressurizing unit.

14. The method of claim 1, wherein using the operational state information to determine whether the powered medical fluid injection device permits the fluid replenishment operation for the first pressurizing unit comprises permitting the fluid replenishment operation if a fluid volume in the first pressuring unit has decreased at least a determined amount since a prior fluid replenishment operation for the first pressurizing unit.

15. A powered medical fluid injection device, comprising:
a first pressurizing unit;
a second pressurizing unit; and
an injector head comprising one or more processors, wherein the injector head is configured to obtain operational state information of the device and use the operational state information to determine whether an automatic fluid replenishment operation is permitted for at least one of the first pressurizing unit and the second pressurizing unit, the operational state information including information, other than a fluid delivery amount for a subsequent injection procedure, to describe an operating state or condition of the device,
wherein if the fluid replenishment operation is permitted for the first pressurizing unit, the injector head is further configured to:
initiate the fluid replenishment operation in order to automatically supply the first pressurizing unit with medical fluid without any manual interaction by a user with the powered medical fluid injection device;
after initiation of the fluid replenishment operation, and while the first pressurizing unit is being supplied with the medical fluid, obtain additional operational state information that is generated based on a manual interaction by the user with a control panel of the powered medical fluid injection device, wherein the additional operational state information specifies that the powered medical fluid injection device is to initiate a new injection procedure using the medical fluid of the first pressurizing unit;
after obtaining the additional operational state information, determine, based on the additional operational state information, that the device will no longer permit the fluid replenishment operation for the first pressurizing unit;
upon determining that the fluid replenishment operation is no longer permitted, automatically terminate, without any manual interaction, the fluid replenishment operation for the first pressurizing unit; and
after terminating the fluid replenishment operation, initiate the new injection procedure, specified by the additional operational state information, using the medical fluid of the first pressurizing unit.

16. The medical fluid injection device of claim 15, further comprising:
at least one air detector that, during operation of the device, is coupled to the first pressurizing unit; and
at least one valve that, during operation of the device, is coupled to the first pressurizing unit.

17. The medical fluid injection device of claim 15, further comprising:
a fluid reservoir holder that, during operation of the device, is coupled to the first pressurizing unit, the fluid reservoir holder being configured to hold a reservoir of medical fluid that is supplied to the first pressurizing unit.

18. The medical fluid injection device of claim 15, wherein the first pressurizing unit comprises a syringe, and wherein the medical fluid comprises at least one of a contrast medium and a diluent.

19. The medical fluid injection device of claim 15, wherein the injector head further configured to:
use the operational state information to determine an amount of the medical fluid to be supplied to the first pressurizing unit.

20. The medical fluid injection device of claim 19, wherein the injector head is configured to determine whether the first pressurizing unit is already filled to capacity when it uses the operational state information to determine the amount of the medical fluid to be supplied to the first pressurizing unit.

21. The medical fluid injection device of claim 20, wherein the determined amount of the medical fluid is equal to zero when the first pressurizing unit is already filled to capacity.

22. The medical fluid injection device of claim 15, wherein the injector head is configured to fill the first pressurizing unit to capacity when it supplies the first pressurizing unit with the medical fluid.

23. The medical fluid injection device of claim 15, wherein the injector head is configured to partially fill the first pressurizing unit when it supplies the first pressurizing unit with the medical fluid.

24. The medical fluid injection device of claim 15, wherein the injector head is configured to determine whether medical fluid is being delivered from the first pressurizing unit when the injector head uses the operational state information to determine whether the powered medical fluid injection device will permit the fluid replenishment operation for the first pressurizing unit.

25. The medical fluid injection device of claim 15, wherein the injector head is configured to use the operational state information to determine whether the powered medical fluid injection device will permit the fluid replenishment operation for the first pressurizing unit by determining whether the medical fluid injection device is delivering medical fluid from the second pressurizing unit.

26. The medical fluid injection device of claim 25, wherein if the medical fluid injection device is currently injecting medical fluid from the second pressurizing unit, the injector head is further configured to determine that the fluid replenishment operation of the first pressurizing unit is permitted.

27. The medical fluid injection device of claim 15, wherein the injector head is configured to supply the first pressurizing unit with the medical fluid if the first pressurizing unit contains less than a specified amount of remaining fluid.

28. The medical fluid injection device of claim 27, wherein the specified amount of remaining fluid comprises a threshold amount that is specified by a user-selectable parameter.

29. The medical fluid injection device of claim 15, wherein the injector head is configured to permit the fluid replenishment operation if at least a determined amount of time has elapsed since a prior injection of medical fluid from the first pressurizing unit.

30. The medical fluid injection device of claim 15, wherein the injector head is configured to permit the fluid replenishment operation for the first pressurizing unit if a fluid volume in the first pressuring unit has decreased at least a determined amount since a prior fluid replenishment operation for the first pressurizing unit.

* * * * *